United States Patent
Margalit

(10) Patent No.: US 9,226,695 B2
(45) Date of Patent: Jan. 5, 2016

(54) DUAL CHAMBER VOLUME MEASUREMENT APPARATUS AND METHODS OF MAKING AND USING THE SAME

(71) Applicant: Near Margalit, Westlake Village, CA (US)

(72) Inventor: Near Margalit, Westlake Village, CA (US)

(*) Notice: Subject to any disclaimer, the term of this patent is extended or adjusted under 35 U.S.C. 154(b) by 220 days.

(21) Appl. No.: 14/184,456

(22) Filed: Feb. 19, 2014

(65) Prior Publication Data

US 2015/0007646 A1    Jan. 8, 2015

Related U.S. Application Data

(60) Provisional application No. 61/842,134, filed on Jul. 2, 2013.

(51) Int. Cl.
  *A61B 5/107* (2006.01)
  *A61B 5/00* (2006.01)

(52) U.S. Cl.
  CPC ............. *A61B 5/1073* (2013.01); *A61B 5/6888* (2013.01); *Y10T 29/49826* (2015.01)

(58) Field of Classification Search
  None
  See application file for complete search history.

(56) References Cited

U.S. PATENT DOCUMENTS

| | | | |
|---|---|---|---|
| 3,769,834 A | 11/1973 | Fletcher et al. | |
| 4,144,749 A * | 3/1979 | Whitmore | G01F 17/00 73/149 |
| 4,144,763 A | 3/1979 | Vogelman | |
| 4,184,371 A | 1/1980 | Brachet | |
| 4,369,652 A | 1/1983 | Gundlach | |
| 5,022,261 A | 6/1991 | Wolfson et al. | |
| 5,052,405 A | 10/1991 | Batchelder | |
| 5,105,825 A | 4/1992 | Dempster | |
| 5,385,069 A | 1/1995 | Johnson, Jr. | |
| 5,450,750 A | 9/1995 | Abler | |
| 5,595,189 A | 1/1997 | Naim et al. | |
| 5,948,977 A | 9/1999 | Siconolfi | |
| 6,345,195 B1 | 2/2002 | Herskowits et al. | |
| 6,702,764 B2 | 3/2004 | Dempster et al. | |
| 6,778,926 B2 | 8/2004 | Dempster | |
| 6,888,640 B2 | 5/2005 | Spina et al. | |
| 7,022,087 B2 | 4/2006 | Dempster et al. | |
| 7,310,999 B2 | 12/2007 | Miller | |
| 2005/0177062 A1* | 8/2005 | Skrabal | A61B 5/0535 600/547 |
| 2007/0062269 A1* | 3/2007 | Miller | A61B 5/103 73/149 |
| 2009/0326396 A1* | 12/2009 | Aliverti | A61B 5/026 600/507 |
| 2010/0245555 A1* | 9/2010 | Talluri | A61B 5/0064 348/77 |

* cited by examiner

*Primary Examiner* — Andre Allen
(74) *Attorney, Agent, or Firm* — Andrew D. Fortney; Central California IP Group, P.C.

(57) ABSTRACT

An apparatus for performing volume measurement of a person, animal or object, and methods of making and using the same are described. The apparatus includes first and second chambers in gaseous communication, first and second pressure sensors that measure the air pressure inside the first and second chambers, a pump configured to move air from or to the first and/or second chambers, and a control system connected to the first and second pressure sensors and the pump. The first and second chambers have a volume that is substantially constant when the internal pressure changes. The control system stores values from the first and second pressure sensors, controls air movement to and/or from the first and second chambers, blocks air transfer between the first and second chambers, and determines the volume of the person, animal or object from pressure measurements before and after an air transfer between the first and second chambers.

20 Claims, 4 Drawing Sheets

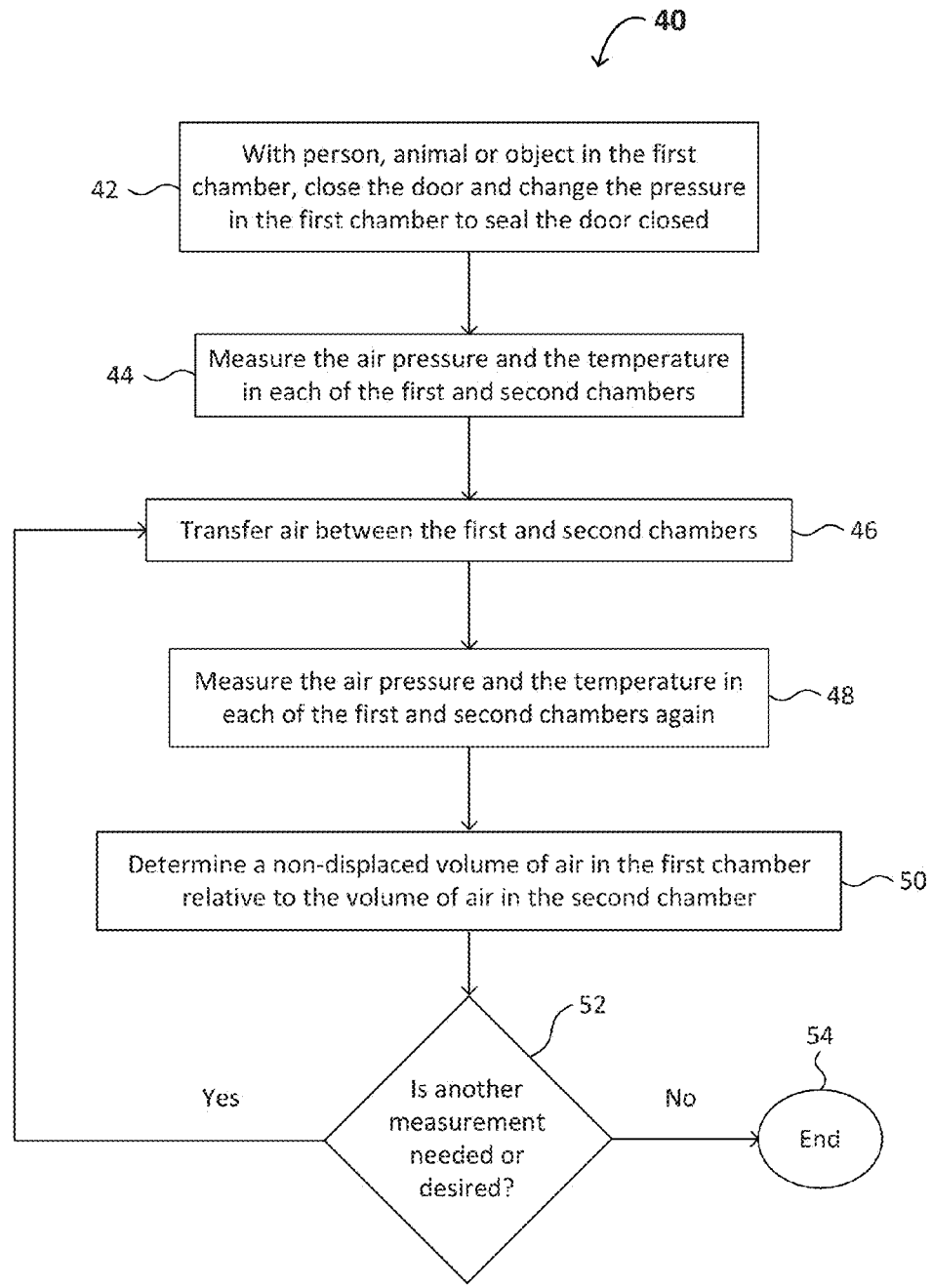

DUAL CHAMBER VOLUME MEASUREMENT APPARATUS AND METHODS OF MAKING AND USING THE SAME

CROSS REFERENCE TO RELATED APPLICATION

This application claims the benefit of U.S. Provisional Patent Application Nos. 61/842,134, filed on Jul. 2, 2013, incorporated herein by reference as if fully set forth herein.

FIELD OF THE INVENTION

The present invention generally relates to the field of volume measurements and/or determinations. More specifically, embodiments of the present invention pertain to a dual chamber apparatus for measuring the volume of an object (e.g., a person or animal), and methods of making such a dual volume chamber and measuring the volume of an object using the same.

DISCUSSION OF THE BACKGROUND

Analysis of body volume may be very useful in a body conscious society to determine progress on reducing body fat and tracking cosmetic appearance. Weight measurement does not provide a complete picture of physical status due to the different densities of muscle cells versus fat cells. Two individuals may have the same weight and height, but have vastly different body volume and composition. Specific measurements such as waist circumference are often used as a proxy to determine changes in size of a person and expected fat composition. However, it may be useful and/or beneficial for an individual to be able to measure the entire volume of the body to determine the progress that exercise or diet may have on body shape and volume. A critical aspect of tracking such performance is the ability to easily and quickly get the measurement one is tracking.

A number of techniques are available on the market to help individuals determine their body composition. The simplest method is measurement of the circumference of specific body parts such as the waist or arms. This provides some information, but does not necessarily provide a complete picture of body volume. A more complete measurement of body volume can be achieved by a technique known as hydrostatic weighing. Here, a person is submerged in an enclosed, water-filled container. The volume of the water that is displaced by the body is equal to the volume of the body. The water volume displaced can be measured with simple geometric formulas, if the container is shaped regularly. Although the above technique can be accurate, it requires a person to go underwater, and may be unpleasant and/or burdensome for individuals. In addition, hydrostatic weighing is not a practical alternative for daily monitoring of body volume.

There are also other techniques to determine body fat percentage, but not necessarily body volume. These include skinfold measurement using calipers in which specific skinfold thicknesses are measured. Finally, bioelectric impedance analysis is another method to estimate body fat. This technique uses high frequency electric current through the body to measure its impedance. Using the different electrical impedances of fat tissue and muscle tissue, an estimate of body fat can be obtained. However, this technique is greatly affected by the state of hydration of the person, and generally has limited accuracy.

Use of air pressure and air displacement to measure volume is referred to as plethysmography. This technique has the potential to achieve the accuracy of hydrostatic weighing, without the inconvenience of the subject going into water. Although this general technique to determine volume has been discussed at least from the 1940s, there has yet to be a solution that is simultaneously accurate, fast, simple, and relatively low-cost. An ideal solution would allow person to get a volume measurement in a fashion similar to a weight scale, simply entering a chamber and getting a volume measurement in a matter of seconds. The current state of the art in such equipment (e.g., the BOD POD® body composition tracking system, available from Cosmed USA, Inc., Concord, Calif.) has not achieved this level of simplicity, speed, and cost. A medical assistant is necessary to operate the system while the person is being measured, and the overall measurement process may be relatively time-consuming. In addition, the user generally must wear a very tight fitting bathing suit during the measurement. The cost of such a system is prohibitively high for daily measurements or personal use by the general public.

Many prior attempts to design such a device require moving mechanical pistons. Others require movable diaphragms to modify the volume of one or both chambers. These techniques limit speed and significantly add to the manufacturing complexity of the system. U.S. Pat. No. 5,450,750 to Abler uses the following equation to determine the volume of air in a reference chamber:

$$P_1 V_1 / T_1 = P_2 (V_1 + \Delta V) / T_2 \qquad (1)$$

A single chamber of varying volume is used to calculate the air displacement in the chamber. In formula (1), $\Delta V$ is the mechanical volume change of the single chamber. Mechanical components used to make such change-in-volume determinations can be expensive, slow, and unreliable, however.

U.S. Pat. No. 5,105,825 to Dempster requires the use of volume changes to compress and rarify the air and measure the resultant pressure changes across two chambers. Again, physical compression and rarefication of air through a volume change requires the chamber walls to be movable mechanically, as opposed to being fixed and/or rigid.

U.S. Pat. No. 4,144,763 to Vogelman describes two chambers, with a valve connecting the two chambers. However, Vogelman uses a single pressure sensor to determine a pressure change. The result is that the pressure must be equal in both chambers before a second pressure measurement can be made. Vogelman introduces Boyle's gas law, which states that for a given mass of gas, the pressure and volume are inversely proportional. By invoking Boyle's law as the primary equation for the measurement, the measurement depends on a single gas mass and its behavior under volume expansion. The use of a single pressure requires the air pressure to fully equalize before a pressure measurement can be useful. However, considering the flow rates and practical behavior of air valves (e.g., the flow rate is proportional to the difference in pressure between the two chambers), the time necessary to equalize pressure between two chambers can be substantial, causing user inconvenience, and more importantly, introducing significant sources of error to the measurement.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

The present invention relates to an apparatus, system and method of volume measurement of objects, people or animals. The present invention advantageously provides a faster and more accurate method to perform such measurements.

For example, the apparatus or system generally comprises a first chamber having a door thereon or affixed thereto, a size sufficient to enclose the person, animal or object, and a first volume when the door is closed; a first pressure sensor that measures an air pressure inside the first chamber; a second, airtight chamber having a second volume; a second pressure sensor that measures an air pressure inside the second chamber; a pump configured to move air from or to at least one of the first and second chambers; and a control system operably connected to the first and second pressure sensors and the pump, the control system being configured to receive and store pressure values from the first and second pressure sensors, control air movement to and/or from the first and second chambers, block air transfer between the first and second chambers, and determine the volume of the person, animal or object in the first chamber from air pressure measurements in the first chamber and the second chamber before and after an air transfer between the first and second chambers, wherein each of the first volume and the second volume changes by less than 5% when the air pressure inside the chamber changes by 5000 Pascals, and an outside pressure on the chamber is fixed or constant. The pressure sensors may be accurate to 1% of atmospheric pressure or more (e.g., to ±1-2 torr, ±1-5 kPa, etc.). The apparatus or system may further comprise first and second temperature sensors configured to measure a temperature of air in the first and second chambers, respectively.

In various embodiments, the apparatus or system may further comprise a first conduit providing gaseous communication between the first chamber and the second chamber, wherein at least one of the pump and a first valve is in the first conduit and is configured to open and close the first conduit (e.g., allow air to pass through or block passage of air to the other chamber). For example, in one implementation, the pump is in the first conduit, is airtight, and is configured to transfer air from the first chamber to the second chamber. In another implementation, the first valve is in the first conduit and is configured to transfer air between the first and second chambers by opening and closing the first conduit.

The system or apparatus may further comprise a gasket, seal or molding between the door and the first chamber. The gasket, seal or molding is configured to make the first chamber airtight when the door is closed and the pressure inside the first chamber changes (e.g., by 3-5%).

The control system may comprise a memory that stores the pressure values from the first and second pressure sensors before and after the air transfer between the first and second chambers. The memory may also store temperature values from the first and second temperature sensors before and after the air transfer between the first and second chambers. The control system may further comprise a non-transitory computer-readable medium that stores a set of instructions to measure the air pressure and the temperature in each of the first and second chambers before and after the air transfer between the first and second chambers, and determine a non-displaced volume of air in the first chamber relative to the volume of air in the second chamber (e.g., from the pressures and temperatures of each of the first and second chambers before and after the air transfer between the first and second chambers). The set of instructions may further comprise instructions to transfer air in a first direction, measure the pressure and temperature inside each of the first and second chambers, transfer air in an opposite direction, and additionally measure the pressure and temperature inside each of the first and second chambers, without the person, animal or object leaving the first chamber during the air transfers or pressure and temperature measurements. For example, the difference in pressure between the first and second chambers after the air transfer between the first and second chambers is at least 500 Pascals.

The system or apparatus may further comprise a scale in the first chamber, configured to measure or determine a weight of the person, animal or object, and/or a graphical user interface (GUI) in the first chamber, operably connected to the control system and configured to receive inputs from a user and display information to the user.

The invention further relates to a method of determining a volume of a person, animal or object, comprising placing the person, animal or object in a first chamber having a size sufficient to enclose the person, animal or object; measuring an air pressure and a temperature in each of the first chamber and a second, airtight chamber in gaseous communication with the first chamber, wherein each of the first and second chambers has a volume that changes by less than 5% when the air pressure inside the respective chamber changes by 5000 Pascals, and an outside pressure on the respective chamber is fixed or constant; transferring air between the first and second chambers; after the air transfer, measuring the pressure and temperature inside each of the first and second chambers again; and determining a non-displaced volume of air in the first chamber relative to the second volume. In one embodiment, transferring air between the first and second chambers comprises opening a valve in a conduit between the first and second chambers, allowing air to flow between the first and second chambers, and closing the valve before the pressure in the first chamber equals the pressure in the second chamber.

In one embodiment, placing the person, animal or object in the first chamber may comprise opening a door on or affixed to the first chamber, closing the door after the person, animal or object enters the first chamber, and removing up to about 10% of the air from the first chamber or adding up to about 10% additional air into the first chamber. The method of determining the volume of the person, animal or object may comprise measuring the pressure and temperature in each of the first and second chambers, transferring the air between the first and second chambers, and measuring the pressure and temperature in each of the first and second chambers again without the person, animal or object leaving the first chamber.

The invention also relates to a method of making a volume measuring apparatus, comprising forming a first chamber having rigid walls, a door thereon or affixed thereto, a size sufficient to enclose the person, animal or object, and a first volume when the door is closed; connecting a second, airtight chamber to the first chamber such that the second chamber is in gaseous communication with the first chamber, the second chamber having a second volume, wherein each of the first volume and the second volume changes by less than 5% when the air pressure inside the chamber changes by 5000 Pascals, and an outside pressure on the chamber is fixed or constant; and placing a first pressure sensor in a first location enabling the first pressure sensor to measure an air pressure inside the first chamber; placing a second pressure sensor in a second location enabling the second pressure sensor to measures an air pressure inside the second chamber; operably connecting a pump configured to move air from or to at least one of the first and second chambers to the second chamber or a conduit between the first and second chambers; and operably connecting a control system to the first and second pressure sensors and the pump, the control system being configured to receive and store pressure values from the first and second pressure sensors, control air movement to and/or from the first and second chambers, block air transfer between the first and second chambers, and determine the volume of the person, animal or object in the first chamber from air pressure measurements in the first chamber and the second chamber before and after an air transfer between the first and second chambers.

The method of making may further comprise placing first and second temperature sensors configured to measure a temperature of air in the first and second chambers, respectively, and/or programming a memory in the control system with a set of instructions to measure the air pressure and the temperature in each of the first and second chambers before and after the air transfer between the first and second chambers, store the pressure and temperature values from the first and second pressure sensors and the first and second temperature sensors before and after the air transfer between the first and second chambers, and determine a non-displaced volume of air in the first chamber relative to the second volume from the pressures and temperatures of each of the first and second chambers before and after the air transfer between the first and second chambers. Additionally or alternatively, the method of making may further comprise forming a gasket, seal or molding on a surface of one of the door and the first chamber facing the other of the door and the first chamber, wherein the gasket, seal or molding is configured to make the first chamber airtight when the door is closed and the pressure inside the first chamber changes (e.g., by 3-5%).

The present invention can achieve new levels of performance, at a reasonable cost and with greater convenience. In embodiments of the current invention, there may be no moving mechanical parts in either of the reference or pressure chambers. Both chambers are rigid and also have fixed volumes, allowing for relatively simple manufacturing techniques. Thus, the formula (1) above highlights a key difference between the current invention and at least some previous work. A secondary benefit of keeping the walls of both chambers fixed is that the expansion or contraction of the air inside the chamber does not do any mechanical work on the chamber, which keeps the heat content of the gas in the chamber substantially constant before and after the flow of gas between the chambers. These and other advantages of the present invention will become readily apparent from the detailed description of various embodiments below.

BRIEF DESCRIPTION OF THE DRAWINGS

FIG. 4 is a flow chart showing an exemplary method of measuring or determining the volume of a person, animal or object.

DETAILED DESCRIPTION

Figure 1:
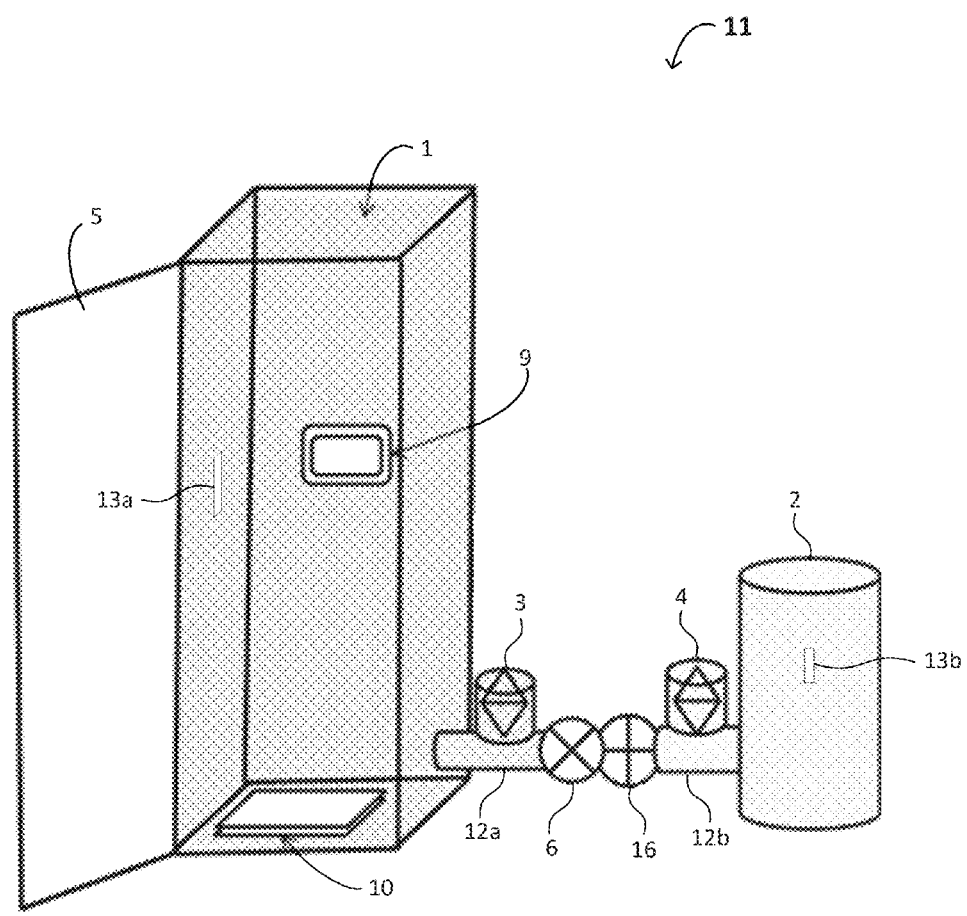
FIG. 1 is a representational view of the invention showing one of the possible embodiments in which an air pump is connecting the two chambers.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

For the sake of convenience and simplicity, the terms "apparatus" and "system" are generally used interchangeably herein, and use of one term generally includes the other, unless the context of its use clearly excludes the other term. Also, for convenience and simplicity, the terms "coupled to," "attached to," "connected to" and "in communication with" (and grammatical variations thereof) may be used interchangeably, and include both the other terms and direct and indirect coupling, connection, or communication unless the context clearly indicates otherwise, but these terms are generally given their art-recognized meanings.

An object of the present invention is to provide an apparatus for measuring whole body volume in a fast and low cost method. By substantially or completely eliminating mechanical components and mechanical motion from components involved in the measurement, the system and method of measuring can be fast and inexpensive. The present apparatus includes two sealed chambers, each with a separate pressure sensor (e.g., a precision barometric pressure sensor) that can accurately and quickly detect the pressure in each chamber. Boyle's law, which is the basis for most previous work, applies to a singular gas mass enclosed in a volume. The law provides the relationship between the pressure in a chamber and changes in volume and/or temperature. In the present invention, Boyle's law is not directly applicable because it uses two chambers with two gas masses, each with an independent pressure. As a result, the two air masses and two separate pressure sensors fundamentally improve user convenience and measurement accuracy, and do not require full equalization of pressure between the chambers.

The invention, in its various aspects, will be explained in greater detail below with regard to exemplary embodiments.

An Exemplary Volume Measuring Apparatus

In one aspect, the present invention relates to an apparatus or system for measuring the volume of a person, animal or object, generally comprising first and second chambers, first and second pressure sensors, a pump, and a control system. The first chamber has a door thereon or affixed thereto. The first chamber also has a volume and/or size that is sufficient to enclose the person, animal or object, and that is substantially constant when the door is closed and the pressure therein changes slightly (e.g., by 1-5% or more). The second chamber is airtight, and has a volume that is substantially constant when the pressure inside the second chamber changes slightly (e.g., by 1-10% or more). When the volume of the chamber does not change under varying pressures, it may be considered to be rigid. For example, a chamber may be considered rigid when the outside pressure on the chamber is fixed or constant, and the volume of the chamber changes by less than 5% for a 5000 Pascal change in the pressure inside the chamber. In further embodiments, the chamber is rigid when the volume of the chamber changes by less than 3%, 2% or 1% (or any other value less than 5%) for a 10 kPa, 20 kPa or 30 kPa (or any other value greater than 5 kPa) change in the pressure inside the chamber.

The first pressure sensor measures the air pressure inside the first chamber, and the second pressure sensor measures the air pressure inside the second chamber. The pump is configured to move air from or to at least one of the first and second chambers (e.g., from the first chamber to the second chamber, or vice versa). The control system is operably connected to the first and second pressure sensors and the pump, and is configured to (i) receive and store pressure values from the first and second pressure sensors, (ii) control air movement to and/or from the first and second chambers, (iii) block air transfer between the first and second chambers, and (iv) determine the volume of the person, animal or object in the first chamber (e.g., from air pressure measurements in the first chamber and the second chamber before and after an air transfer between the first and second chambers).

In various embodiments, the present apparatus is useful in medical offices, physical therapy and/or training facilities, professional and amateur athletic training facilities for measuring the volume and/or calculating a percentage or other proportion of body fat of a person. The present apparatus may be useful in veterinary medicine, on a ranch or farm, or in animal husbandry for measuring the volume and/or calculating a percentage or other proportion of body fat of an animal. Also, certain objects may not be regularly shaped and/or submersible in water, and the present apparatus is useful for measuring such objects, among other objects and/or uses.

FIG. 1 shows an embodiment of the present body volume measurement apparatus 11. The subject enters and exits a rectangular chamber 1 using a door 5. The chamber is rectangular in the embodiment 11 shown, but is can have other shapes and/or cross-sections as well (e.g., cylindrical, semi-cylindrical, hexagonal, octagonal, pentagonal, semi-circular, combinations thereof, etc.). The rigidity of a chamber generally improves with increasing roundness, so for a chamber of given volume and the same material(s), a semi-cylindrical chamber is more rigid than a rectangular chamber, and a cylindrical chamber is more rigid than a semi-cylindrical chamber. A spherical chamber may be ideal for rigidity, but is generally impractical for use as the subject chamber. The height, width and depth of the subject chamber 1 as shown is constant and/or uniform across the chamber, but are not required to be so. However, the walls of the subject chamber 1 and the door 5 are stiff and/or rigid (e.g., they do not noticeably bend under low pressure and/or slight vacuum). Closing the door 5 generally creates an airtight seal of the chamber and forms the primary chamber in the invention. For example, an airtight seal or molding may be between the subject chamber 1 and the door 5 (e.g., on the front edges or surface of the subject chamber 1 or around the periphery of the door 5) that compresses by a known amount at one or more predetermined pressures in the subject chamber 1.

A precise pressure sensor 3 can be read electronically, and the pressure readings from subject chamber 1 can be stored in an electronic memory (e.g., in a desktop, laptop, tablet, or handheld computer, in a volatile and/or non-volatile memory electronically connected to a controller or other logic that controls operations of the apparatus 11, performs calculations on the information stored in the memory, and displays messages, readings and/or the results on a graphical user interface 9, etc.). The pressure reading from pressure sensor 3 is the pressure in chamber 1, as the sensor is directly connected to the air in subject chamber 1.

The apparatus includes a secondary chamber 2 in fluid and/or gaseous communication with the subject chamber 1. The secondary (or reference) chamber 2 generally has a volume that is not more than 20-25% of the volume of the first chamber. In various embodiments, the volume of the second chamber is from 5-20% (e.g., 8-15%) of the volume of the first chamber. The secondary chamber 2 also has a precise pressure sensor 4 operably connected thereto. An electronic valve 6 is in a conduit 12a-b between the subject chamber 1 and the secondary chamber 2. The electronic valve 6 can isolate the air and/or block or close the air flow between the subject chamber 1 and the secondary chamber 2. An airtight air pump 16 can move air from chamber 1 to chamber 2, or from chamber 2 to chamber 1. The pump 16 can be or comprise any device that moves air into or out of a chamber, and in some cases, when the pressure difference between the input and the output of the pump is zero or negative (e.g., the pump moves air from a space of relatively low pressure to a space of relatively high pressure). In some cases, the electronic valve value 6 is not necessary when the air pump 16 can sufficiently isolate the air between chamber 1 and chamber 2.

The subject chamber 1 and the secondary chamber 2 may each include a temperature sensor 13a and 13b, respectively, configured to measure the temperature (e.g., in ° C.) in each of the subject chamber 1 and the secondary chamber 2. Although the temperature sensors 13a and 13b can be placed in any location in the chambers 1 and 2, the temperature sensors 13a and 13b may be placed in locations that enable facile and/or rapid determination of the true and/or average temperature of the air in the corresponding chamber, or of a representative temperature in the chamber that reflects an accurate temperature of the air in the chamber relative to the other chamber. The subject chamber 1 and the secondary chamber 2 may each further include a fan (not shown) that circulates the air in the corresponding chamber and facilitates a relatively rapid equilibration of the temperature in the chamber. In one implementation, the fan operates for a limited and/or predetermined length of time after an air transfer event (e.g., to minimize the heat added to the chamber and/or system by the fan).

A graphical user interface (GUI) 9 can be included in the apparatus 11. A subject may directly interface with the user interface 9 to initiate a measurement and obtain measurement results, which may include body volume, weight, body fat content (e.g., as a percentage of body weight), etc. An electronic control system (not shown, but generally behind or enclosed within the housing of the GUI 9) may control operations of the apparatus 11 and/or perform calculations necessary to determine body volume, body fat content, weight, etc. An optional weight scale 10 inside the subject chamber 1 allows for simultaneously measuring the subject's weight along with the subject's body volume. Weight and volume can be used to determine a person's or animal's density, which in turn can be used to determine body composition, such as fat percentage.

The present apparatus 11 uses dual rigid airtight chambers 1, 2 with a high precision pressure sensor 3, 4 in each chamber. Transfer of a portion of the air from one chamber to the other, along with measuring the change of pressure in each chamber, allows for a calculation of the relative volume of the chambers. The two rigid airtight chambers 1, 2 of known volume are connected by a conduit 12a-b that can be closed using a pump 16 and/or a valve 6. The chamber 1 is referred to as the subject or user chamber, and the other chamber 2 is known as the reference chamber.

The user chamber 1 encloses the subject. The volumes of both chambers 1, 2 without the subject enclosed are measured or calculated as part of the manufacturing or calibration process. A subject displaces a certain amount of volume from the user chamber 1 when he/she enters the chamber 1 and closes the door 5. The remaining air volume in the user chamber 1 is calculated using methodology disclosed herein. Thus, the volume of the subject is calculated and presented on the GUI 9 as the volume of the user/subject (primary) chamber 1 without the subject minus the volume of air in the user/subject chamber 1 with the subject inside. The relative volume calculation of the user/subject chamber 1 with subject inside relative to volume of the reference (secondary) chamber 2 is done using a technique disclosed herein. Although volume measurements using air displacement have been known for decades, and there is one commercially available system that uses air displacement, the present invention allows for a low-cost, fast, accurate and practical system and method to achieve volume measurements using air displacement.

Each of the chambers 1, 2 has a certain amount of air (or air mass) at the start of the measurement, and each chamber 1, 2 has an equilibrium pressure that may be described by the ideal gas law (e.g., pV=nRT). The pressure in each chamber is measured independently using the two precision pressure sensors 3, 4. The apparatus 11 uses an air transfer event which transfers air mass from one chamber to the other, and then re-isolates the two chambers 1, 2.

After the air transfer event, new pressure measurements are made in the two chambers 1, 2. Using a mathematical technique as disclosed herein, the relative volumes of both chambers 1, 2 can be calculated using the four pressure measurements described above (i.e., in both chambers, before and after the air mass transfer event).

The air transfer event may occur in any of several variations disclosed herein, among other possibilities. In one embodiment, the airtight air pump 16 directly pumps or pushes air between the primary chamber 1 and the secondary chamber 2 through the conduit 12a-b. A measurement is made before the pump 16 is engaged. The pump 16 is then engaged, pushing air between the chambers 1, 2 (e.g., from the user chamber 1 and the reference chamber 2) and altering the air pressure in both chambers. In general, a mass of air sufficient to change the pressure in the user chamber 1 by 10-100 torr (e.g., to a pressure of from about 0.9 to about 1.1 atm, from about 0.92 to about 0.98 atm, or from about 1.02 to about 1.08 atm, or any value within those ranges other than the starting pressure [e.g., 1 atm or 760 torr]) may be moved to or from the used chamber 1. When the air transfer event is complete, a second set of measurements for the volume calculations is made on the changed air pressures in both chambers.

Alternatively, a different embodiment involves adding air to (e.g., pumping air into) or removing air from (e.g., pumping air from) one of the chambers, such that the air pressure in each of the two chambers 1, 2 is not equal. Once the air pressure is different in both chambers, the initial pressure readings can be made. Thereafter, the valve 6 between the two chambers 1, 2 is opened, creating a rush of air between the chambers 1, 2 and transferring air (e.g., an air mass). The valve 6 can then be closed, completing the air transfer event. New pressure readings can be made in both chambers 1, 2. Because of the availability of pressure sensors 3, 4 in both chambers, it is not necessary for the air pressure to equalize between both chambers 1, 2 before the valve 6 is closed. Previous attempts at solving this system using two chambers required the pressure to fully equalize between both chambers, since a single pressure value for both chambers is used in the calculation. This limitation is significant, because the time needed to fully equalize the pressure the two chambers connected by a conduit and a valve can be relatively long. The length of time for pressure equilibration may cause inconvenience to the user, and may also add significant error to the measurement, due to practical limitations such as leaks and temperature changes during the equalization process. Thus, the present invention allows for an extremely fast air transfer event that increases user convenience and improves accuracy.

The following mathematical equations and/or calculations show how a transfer of a portion of the air from one chamber to the other chamber allows for the calculation of the relative volumes of both chambers. In the following equations, PA1 is the initial pressure in the user chamber 1, PA2 is the pressure in the user chamber 1 after air the air transfer event, PB1 is the initial pressure of the reference chamber 2, PB2 is the pressure in the reference chamber 2 after the air transfer event, VA is the volume of the user chamber 1, VB is the volume of the reference chamber 2, $n_{A1}$ and $n_{A2}$ are the number of air molecules in the user chamber 1 before and after the air transfer event, respectively, $n_{B1}$ and $n_{B2}$ are the number of air molecules in the reference chamber 2 before and after the air transfer event, respectively, TA1 and TA2 are the temperatures in the user chamber 1 before and after the air transfer event, and TB1 and TB2 are the temperatures in the reference chamber 2 before and after the air transfer event. R is the universal or ideal gas constant, 8.314 J/K·mol. The number of molecules of air transferred between the chambers 1 and 2 is Δn.

The ideal gas law for the user (primary) chamber 1 before the air transfer event is:

$$PA1 \times VA = n_{A1} \times R \times TA1 \qquad [2]$$

The ideal gas law for the reference (secondary) chamber 2 before the air transfer event is:

$$PB1 \times VB = n_{B1} \times R \times TB1 \qquad [3]$$

The equation that shows the amount of air transferred between the chambers 1, 2 is:

$$\Delta n = nA2 - nA1 = nB2 - nB1 \qquad [4]$$

The ideal gas law for the user (primary) chamber 1 after the air transfer event is:

$$PA2 \times VA = n_{A2} \times R \times TA2 \qquad [5]$$

The ideal gas law for the reference (secondary) chamber 2 after the air transfer event is:

$$PB2 \times VB = n_{B2} \times R \times TB2 \qquad [6]$$

Solving these equations using relatively simple algebra results in an equation of the relative volume of air in the user chamber 1 and the reference chamber 2. It is important to note that both VA and VB do not change during this process.

$$VA/VB = (PB2/TB2 - PB1/TB1)/(PA2/TA2 - PA1/TA1) \qquad [7]$$

A key point of these equations is that as long as there is no leakage of molecules from the two chambers, the relationship between VA and VB can be calculated using the before and after pressure in each chamber 1, 2. This is true regardless of the number of molecules that are transferred between the chambers 1, 2. This means that the present apparatus and method of volume measurement do not require a precise method to measure the amount of air transferred between the chambers to get a determination of the volume of the chambers.

An example calculation is as follows. VA without subject inside is 1000L, and VB is 75.7L. One example of the reference chamber 2 can be a rigid (e.g., steel) 20 gallon tank (e.g., part number FIR9277, manufactured by Firestone Rubber and Chemical Co., and commercially available from a large number of retailers, resellers and/or distributors). The reference chamber 2 may have an internal and/or external coating (e.g., enamel, latex, etc.). The user chamber 1 can be a custom acrylic rectangular box or tube that is cut (e.g., in half or otherwise) to allow the user to enter the chamber 1. The starting temperature for both chambers 1 and 2 is 25° C., or 298 K. The starting pressure PB1 of the reference chamber 2 is 30 kPa, and the starting pressure PA1 of the user chamber 1 is 97 kPa. After the air transfer event (e.g., opening and closing the electronic valve 6), the pressure in the reference chamber 2 is 80 kPa, and the pressure in the user chamber 1 drops from 97 kPa to 92.3 kPa. The temperature of the air in the reference chamber 2 increases due to compression, and goes from 298K to 338K. The temperature of the air in the user chamber 1 decreases due to rarefication, and goes from 298K to 296K. Using Equation [7] above, the volume of chamber A under these conditions is confirmed to be 1000 L.

Now repeating this process, but with a person inside the user chamber 1, we get new values for PA2 and PB2. For simplicity, the same initial pressures and the same initial and final air temperatures inside the chambers 1 and 2 are assumed. The new values for PA2 and PB2 are 92.0 kPa and 79.9 kPa. Putting these new numbers into the calculation (Equation [7]) results in a VA value of 923.7 L. The difference between the 1000L unoccupied volume of the user chamber 1 and the 923.7 L volume with a user inside is the volume of the person, which in this example is 76.3 L. The methods to get the exact temperature and pressure measurements to get the necessary precision may be intricate and/or closely controlled. In addition, it may be essential to ensure that the door is both sealed without a leak and is completely or substantially completely rigid, which may introduce some complexity. These issues are described at least in part in a separate patent application filed on the same day as the present application (see U.S. Provisional Patent Application No. 61/941,770, filed Feb. 19, 2014 ).

In one embodiment, air is removed from or pumped out of the reference chamber 2 so that it starts with a pressure lower than the user chamber 1, which generally has an initial pressure (e.g., with the user inside) slightly below the surrounding ambient, typically about 0.93-0.97 atm, 94-98 kPa, or 720-740 ton, to ensure that the door 5 stays tightly closed. At such small reduced pressures, the user is not in any danger of oxygen deprivation. The air is removed from or pumped out of the reference chamber 2 using a conventional vacuum pump (such as model no. MS750W, available from Nimbo Motors), then the slight vacuum is formed in the user chamber 1 by opening the valve 6 until the desired pressure is attained, and the valve 6 is then closed. The valve 6 may be or comprise an electronic solenoid valve, such as an ASCO high flow solenoid valve. Additional air may be removed or pumped from the reference chamber 2, is desired. A precise measurement of the pressure in both chambers 1 and 2 is taken and stored in electronic memory before transferring air from the user chamber 1 to the reference chamber 2. The valve 6 is then activated/opened, allowing air to flow between the two chambers 1 and 2. The valve 6 is then closed or shut, allowing new pressure equilibriums to exist in the two chambers. The pressure in the user chamber 1 does not necessarily equal the pressure in the reference chamber 2. Finally, the pressure in both chambers 1 and 2 is measured again. The flow rate of air between the chambers 1, 2 is faster when the difference in pressure between the two chambers is relatively large, so stopping the air transfer before the pressure in both chambers is fully equalized can save a significant amount of time.

In an alternative embodiment, an airtight air pump 16 is connected hermetically in the conduit 12a-b between the user (primary) and reference (secondary) chambers 1 and 2. The valve 6 is not necessarily present. A measurement is taken (optionally after pulling a slight vacuum in the user chamber 1 as described in the previous paragraph) of the air pressures before the pump 16 is activated. The pump 16 then is turned on, forcing air from one chamber to the other and causing a differential pressure to occur in both chambers 1 and 2 relative to the original pressure values in the chambers 1 and 2. New measurements can be taken with the new pressure readings in both chambers 1 and 2. A series of values can be measured as the pump 16 continues to change the value of the pressures through the transfer of air between the chambers 1 and 2. In this embodiment, since air may be continuously removed from the user chamber 1, there may be a pressure-activated shut-off switch in the pump 16, configured to automatically turn the pump 16 off when the pressure in the user chamber 1 reaches a predetermined value, for example 0.9 atm, 90 kPa, or 700 ton.

A Second Exemplary Volume Measuring Apparatus

Figure 2:
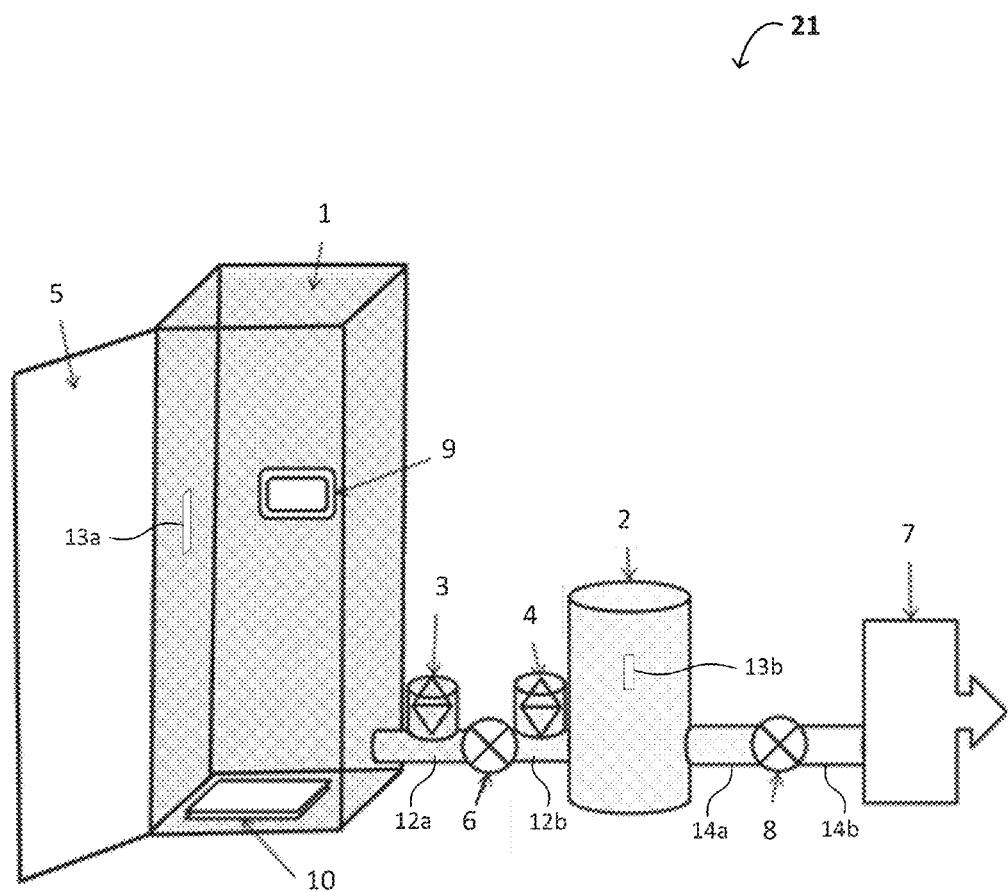
FIG. 2 is a representational view of the invention showing one of the possible embodiments using a vacuum pump attached to the secondary chamber.

FIG. 2 shows a slightly different embodiment of the present apparatus 21, where some of the components may be added, removed or changed, but the basic principle(s) of measurement remain the same or substantially the same. In the apparatus 21 of FIG. 2, rather than directly transferring air between the user chamber 1 and the reference chamber 2 using a pump, one of the chambers (e.g., reference chamber 2) has air removed or added using an air transfer device 7. In various implementations, depending on whether air is removed or added, the air transfer device may be a vacuum pump or an air compressor.

In the exemplary apparatus 21, a valve 6 (e.g., an electric valve) may isolate the air and/or close or block the first conduit 12a-b between chambers 1 and 2. Valve 8 in a second conduit 14a-b is opened to allow air transfer device 7 to transfer air into or out of the reference chamber 2. This creates an air pressure in the reference chamber 2 that is different from the pressure in user chamber 1. Once the initial air pressure differential is established, then valve 8 is closed so that chamber 2 has a specific pressure, mass (e.g., number of air molecules/atoms) and volume. The pressure in both chambers 1 and 2 is measured using the pressure sensors 3 and 4. At this point, the air transfer is accomplished between chambers 1 and 2 by opening valve 6. Because both chambers are at different pressures, air flows from the higher pressure chamber (e.g., the user chamber 1) to the lower pressure chamber (e.g., the reference chamber 2). This in effect acts like a pump pushing air from one chamber to the other. Once a sufficient amount of air flows from one chamber to the other, the valve 6 is closed. The result is new pressure equilibriums in chambers 1 and 2. The new pressure values can be measured by pressure sensors 3 and 4.

Using the mathematical formulas (e.g., Equations [7]) and the ideal gas law separately in both chambers 1 and 2, the air volume in the user chamber 1 can be determined. Knowing the original full volume of the user chamber 1 then allows for the calculation and display of the volume of subject.

Other embodiments may include evacuating or pressurizing chamber 1, or even both chambers 1 and 2, to different values in order to achieve air flow between the chambers and enable differential pressure measurements. Also, conducting a plurality of different measurements under different pressure and/or temperature conditions in either or both chambers enables more accurate volume calculations, as an average value over a variety of test/measurement conditions is more likely to be accurate than the value from a single calculation.

A Third Exemplary Volume Measuring Apparatus

Figure 3:
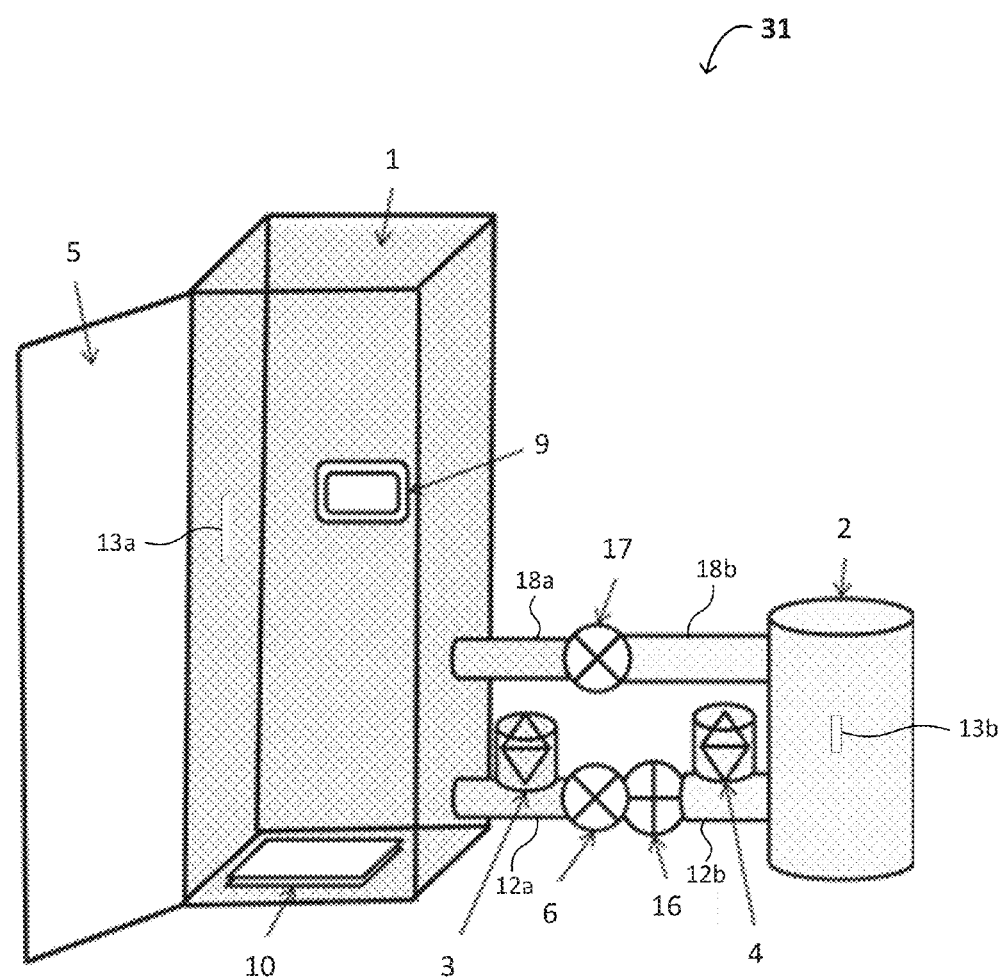
FIG. 3 is a representation view of the invention showing one of the possible embodiments using a combination of an air pump to create air transfer event in one direction and a valve to create an air transfer event in the opposite direction.

FIG. 3 shows a third embodiment 31 of the present apparatus. In the apparatus 31, air transfer events can occur either from user chamber 1 to reference chamber 2 through the direct air pump 16, or from reference chamber 2 to user chamber 1 through a valve 17 in a second conduit 18a-b. In the apparatus 31, an initial air transfer event occurs as before with the air pump 16, which can pressurize or evacuate the user chamber 1. For example, if the door 5 swings into the user chamber 1, an increase in pressure in the user chamber 1 resulting from additional air being pumped into the user chamber 1 by the air pump 16 can seal the door closed.

Measurements of the volume of air in the user chamber 1 (i.e., after obtaining both before and after pressure readings in chambers 1 and 2) can be initiated in at least two ways. One way is to create an additional air transfer event from user chamber 1 to reference chamber 2 using the air pump 16. Another way is to open the valve 17, which allows pressurized air to rush from the reference chamber 2 to the user chamber 1. Each time there is an air transfer event, a new pressure measurement can be made, and the subject's volume can be calculated.

The apparatus 31 allows for the air pressure in either chamber 1, 2 to remain closer to atmospheric pressure, because the pressure in either chamber can be raised and/or lowered in successive air transfer events, and additional pressure measurements made. This is useful when the subject (e.g., a human being) is sensitive to pressure changes (e.g., a sudden pressure change may cause pain in the subject's inner ear). Also, a plurality of different volume calculations under different conditions (e.g., pressure and/or temperature in either or both chambers) enables increased accuracy, as an average value over a variety of test/measurement conditions is more likely to be accurate than the value from a single calculation.

An Exemplary Method and Software Program for Determining a Volume of an Object

A further aspect of the invention relates to a method of determining a volume of a person, animal or object, comprising placing the person, animal or object in a first chamber, measuring an air pressure and a temperature in each of the first chamber and a second, airtight chamber in gaseous communication with the first chamber, transferring air between the first and second chambers, then after the air transfer, measuring the pressure and temperature inside each of the first and second chambers again, and determining a non-displaced volume of air in the first chamber relative to the volume of the second chamber. In one embodiment, transferring air between the first and second chambers comprises opening a valve in a conduit between the first and second chambers, allowing air to flow between the first and second chambers, and closing the valve before the pressure in the first chamber equals the pressure in the second chamber. The first chamber has a volume and/or size that is sufficient to enclose the person, animal or object, and that is substantially constant when the pressure inside the first chamber changes (e.g., by 1-5% or more). The second chamber has a volume that is substantially constant when the pressure inside the second chamber changes (e.g., by 1-10% or more).

FIG. 4 shows a flow chart that outlines an exemplary method 40 of measuring or determining a volume of a person, animal or object. The method starts when the person enters the first chamber, or the animal or object is placed in the first chamber. If the system or apparatus has a GUI outside the first chamber, then the user does not need to enter the first chamber.

At 42, with the person, animal or object in the first chamber, the door is closed, and the pressure in the first chamber is changed. The pressure may be increased or decreased by 2-5% (e.g., about 3%) to seal the door closed. When the door is mounted on and opens to the inside of the chamber, the pressure is increased to seal the door closed. When the door is mounted on and opens to the outside of the chamber, the pressure is decreased to seal the door closed. The pressure in the second chamber may be changed by a different amount (e.g., by more than 10%, or at least 2-3× more than the first chamber), generally in the same direction (e.g., either increased or decreased) as the first chamber. Alternatively, the pressure in the second chamber may be left unchanged, for example if the pressure in the first chamber is changed by a relatively large amount (e.g., 5-10%). In a further alternative, if the door can be secured in an airtight manner (e.g., with one or more physical latches that apply pressure to the door against the airtight seal or molding between the door and the chamber wall[s]), the first chamber can remain at ambient or atmospheric pressure, and the pressure in the second chamber can be changed (e.g., by 10-20% or more).

At 44, a first measurement of the air pressures and the temperatures in each of the first and second chambers is made. The pressure and temperature values are recorded (e.g., by storing in a memory in the system/apparatus). Air is then transferred from the chamber having a higher pressure to the chamber having a lower pressure at 46. This may be done by opening a valve in a conduit between the first and second chambers, or by opening a passage in a pump configured to transfer air between the two chambers, as described herein. In general, an amount of air is transferred that is sufficient to change the pressures in each of the chambers by an amount exceeding or significantly exceeding the possible error in the pressure measurements. At 48, a second measurement of the air pressures and the temperatures in each of the first and second chambers is made and recorded. At 50, the non-displaced volume of air in the first chamber (i.e., the volume of air in the first chamber not occupied or displaced by the person, animal or object) is determined or calculated. In one embodiment, the control system includes a microcontroller or other circuit with an arithmetic logic unit capable of calculating the relative air volume ratio between the two chambers using the pressure and temperature measurements, then calculating the volume of the person, animal or object using relatively simple algebra. In a further embodiment, the control system is capable of calculating the percentage or other amount of body fat of a person or animal in the first chamber. In an even further embodiment, the method 40 includes weighing the person or animal in the chamber, and calculating an amount of weight that the person or animal should lose or gain.

At 52, a determination is made as to whether another measurement is needed or desired (e.g., to increase the accuracy of the volume calculation/determination). If so, the method returns to 46, and another transfer of air (e.g., from the chamber having a relatively high pressure to a chamber having a relatively low pressure) is made. If desired, the chamber having a relatively low pressure may have some air removed from it (e.g., by pumping or evacuation, or in the case of an overpressure, bleeding or leaking air out of the chamber) before the additional air transfer at 46. The air pressures and temperatures in each of the first and second chambers are measured again and recorded and 48, and at 50, the non-displaced volume of air in the first chamber is determined or calculated again. An average volume of the person, animal or object may then be calculated, if desired. However, if no further measurements are needed or desired, the method 40 ends at 54.

An Exemplary Method of Making a Volume Measuring Apparatus

The present invention further relates to method of making a volume measuring apparatus, comprising forming a first chamber, connecting a second chamber to the first chamber such that the second chamber is in gaseous communication with the first chamber, placing first and second pressure sensors in locations enabling the pressure sensors to measure an air pressure inside the first and second chambers, operably connecting a pump to the apparatus, and operably connecting a control system to the first and second pressure sensors and the pump. The first chamber has rigid walls, a door thereon or affixed thereto, a size sufficient to enclose the person, animal or object, and a first volume that is substantially constant when the door is closed and the pressure inside the first chamber changes (e.g., by 1-5% or more). The second chamber is airtight and has a second volume that is substantially constant when the pressure inside the second chamber changes (e.g., by 1-10% or more). The pump is configured to move air from or to at least one of the first and second chambers, or through a conduit between the first and second chambers. The control system is configured to receive and store pressure values from the first and second pressure sensors, control air movement to and/or from the first and second chambers, block air transfer between the first and second chambers, and determine the volume of the person, animal or object in the first chamber (e.g., from air pressure measurements in the first chamber and the second chamber before and after an air transfer between the first and second chambers).

This method may further comprise placing first and second temperature sensors configured to measure a temperature of air in the first and second chambers, respectively. Both the temperature sensors and the pressure sensors may be placed in the corresponding chamber, or in a conduit, a sealable opening, or other structure in gaseous communication with the chamber. Preferably, the temperature sensors and the pressure sensors are in a location in which they can directly measure the temperature or pressure, respectively, and without requiring a relatively long time for the temperature or pressure to equalize throughout the chamber.

This method may also further comprise programming a memory in the control system with a set of instructions to: (i) measure the air pressure and the temperature in each of the first and second chambers before and after the air transfer between the first and second chambers, (ii) store the pressure and temperature values from the first and second pressure sensors and the first and second temperature sensors before and after the air transfer between the first and second chambers, and/or (iii) determine a non-displaced volume of air in the first chamber relative to the second volume from the pressures and temperatures of each of the first and second chambers before and after the air transfer between the first and second chambers, for example as described herein. Naturally, other functions and data may be stored in the memory of the control system, as described herein.

Additionally or alternatively, the method of making may further comprise forming or attaching a gasket, seal or molding on a surface of one of the door and the first chamber, wherein the gasket, seal or molding is configured to make the first chamber airtight when the door is closed and the pressure inside the first chamber changes (e.g., by 1-5%). Generally, the surface on which the gasket, seal or molding is formed or attached faces an opposing surface of the other of the door and the first chamber. For example, when the door opens to the outside, the gasket, seal or molding is formed on or attached to an outer surface of the chamber (e.g., in a region that overlaps with a peripheral portion of the door) or the peripheral portion of the inner surface of the door. When the door opens to the inside, the gasket, seal or molding is formed on or attached to an inner surface of the chamber (e.g., in a region that overlaps with a peripheral portion of the door) or the peripheral portion of the outer surface of the door.

Naturally, the method of making can further include attaching, affixing and/or forming other components described herein to, on or in the system, in various ways consistent with the present disclosure and/or the knowledge in the art.

CONCLUSION/SUMMARY

Thus, the present invention provides an apparatus or system for measuring a volume of a person, animal or object, a method of measuring a volume of a person, animal or object, and a method of making such a volume measuring apparatus or system. The present invention can achieve new levels of performance, at a reasonable cost and with greater convenience. In embodiments of the current invention, there may be no moving mechanical parts in either or both of the reference and user chambers. Both chambers are rigid and have fixed volumes, allowing for relatively simple manufacturing techniques. The volumes of the chambers do not vary noticeably, even though the pressures in the chambers may vary significantly. Thus, a relatively simple calculation (see Equation [7] above) enables facile and relatively inexpensive volume measurements of people, animals, or other objects that may not be so easy to measure. A secondary benefit of keeping the walls of both chambers fixed is that the expansion or contraction of the air inside the chamber does not do any mechanical work on the chamber, which keeps the heat content of the gas in the chamber substantially constant before and after the flow or transfer of gas between the chambers.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A system or apparatus for measuring a volume of a person, animal or object, comprising:
   a) a first chamber having a door thereon or affixed thereto, a size sufficient to enclose the person, animal or object, and a first volume when the door is closed;
   b) a first pressure sensor that measures an air pressure inside the first chamber;
   c) a second, airtight chamber having a second volume;
   d) a second pressure sensor that measures an air pressure inside the second chamber;
   e) a pump configured to move air from or to at least one of the first and second chambers; and
   f) a control system operably connected to the first and second pressure sensors and the pump, the control system being configured to receive and store pressure values from the first and second pressure sensors, control air movement to and/or from the first and second chambers, block air transfer between the first and second chambers, and determine the volume of the person, animal or object in the first chamber from air pressure measurements in the first chamber and the second chamber before and after an air transfer between the first and second chambers, wherein each of the first volume and the second volume changes by less than 5% when the air pressure inside the chamber changes by 5000 Pascals, and an outside pressure on the chamber is fixed or constant.

2. The system or apparatus of claim 1, further comprising a first conduit providing gaseous communication between the first chamber and the second chamber, and at least one of the pump and a first valve is in the first conduit and is configured to open and close the first conduit.

3. The system or apparatus of claim 2, wherein the pump is in the first conduit, is airtight, and is configured to transfer air from the first chamber to the second chamber.

4. The system or apparatus of claim 2, wherein the first valve is in the first conduit and is configured to transfer air between the first and second chambers by opening and closing the first conduit.

5. The system or apparatus of claim 1, further comprising a gasket, seal or molding between the door and the first chamber, wherein the gasket, seal or molding is configured to make the first chamber airtight when the door is closed and the pressure inside the first chamber changes by 3-5%.

6. The system or apparatus of claim 1, wherein the control system comprises a memory that stores the pressure values from the first and second pressure sensors before and after the air transfer between the first and second chambers.

7. The system or apparatus of claim 6, further comprising first and second temperature sensors configured to measure a temperature of air in the first and second chambers, respectively, and the memory stores temperature values from the first and second temperature sensors before and after the air transfer between the first and second chambers.

8. The system or apparatus of claim 7, wherein the control system further comprises a non-transitory computer-readable medium that stores a set of instructions to measure the air pressure and the temperature in each of the first and second chambers before and after the air transfer between the first and second chambers, and determine a non-displaced volume of air in the first chamber relative to the second volume.

9. The system or apparatus of claim 8, wherein the set of instructions further comprises instructions to transfer air in a first direction, measure the pressure and temperature inside each of the first and second chambers, transfer air in an opposite direction, and additionally measure the pressure and temperature inside each of the first and second chambers, without the person, animal or object leaving the first chamber during the air transfers or pressure and temperature measurements.

10. The system or apparatus of claim 1, wherein a difference in pressure between the first and second chambers after the air transfer between the first and second chambers is at least 500 Pascals.

11. The system or apparatus of claim 1, where the pressure sensors are accurate to at least one percent of atmospheric pressure.

12. The system or apparatus of claim 1, further comprising a scale in the first chamber, the scale being configured to measure or determine a weight of the person, animal or object.

13. The system or apparatus of claim 1, further comprising a graphical user interface in the first chamber, the graphical user interface being operably connected to the control system and configured to receive inputs from a user and display information to the user.

14. A method of determining a volume of a person, animal or object, comprising:
  a) placing the person, animal or object in a first chamber having a size sufficient to enclose the person, animal or object;
  b) measuring an air pressure and a temperature in each of the first chamber and a second, airtight chamber in gaseous communication with the first chamber, wherein each of the first and second chambers has a volume that changes by less than 5% when the air pressure inside the respective chamber changes by 5000 Pascals, and an outside pressure on the respective chamber is fixed or constant;
  c) transferring air between the first and second chambers;
  d) after the air transfer, measuring the pressure and temperature inside each of the first and second chambers again; and
  e) determining a non-displaced volume of air in the first chamber relative to the second volume.

15. The method of claim 14, wherein transferring air between the first and second chambers comprises opening a valve in a conduit between the first and second chambers, allowing air to flow between the first and second chambers, and closing the valve before the pressure in the first chamber equals the pressure in the second chamber.

16. The method of claim 14, wherein placing the person, animal or object in the first chamber comprises opening a door on or affixed to the first chamber, closing the door after the person, animal or object enters the first chamber, and removing up to about 10% of the air from the first chamber or adding up to about 10% additional air into the first chamber.

17. The method of claim 14, wherein the pressure and temperature in each of the first and second chambers is measured, the air is transferred between the first and second chambers, and the pressure and temperature in each of the first and second chambers is measured again without the person, animal or object leaving the first chamber.

18. A method of making a volume measuring apparatus, comprising:
  a) forming a first chamber having rigid walls, a door thereon or affixed thereto, a size sufficient to enclose the person, animal or object, and a first volume when the door is closed;
  b) connecting a second, airtight chamber to the first chamber such that the second chamber is in gaseous communication with the first chamber, the second chamber having a second volume, wherein each of the first volume and the second volume changes by less than 5% when the air pressure inside the chamber changes by 5000 Pascals, and an outside pressure on the chamber is fixed or constant; and
  c) placing a first pressure sensor in a first location enabling the first pressure sensor to measure an air pressure inside the first chamber;
  d) placing a second pressure sensor in a second location enabling the second pressure sensor to measures an air pressure inside the second chamber;
  e) operably connecting a pump configured to move air from or to at least one of the first and second chambers to the second chamber or a conduit between the first and second chambers; and
  f) operably connecting a control system to the first and second pressure sensors and the pump, the control system being configured to receive and store pressure values from the first and second pressure sensors, control air movement to and/or from the first and second chambers, block air transfer between the first and second chambers, and determine the volume of the person, animal or object in the first chamber from air pressure measurements in the first chamber and the second chamber before and after an air transfer between the first and second chambers.

19. The method of claim 18, further comprising placing first and second temperature sensors configured to measure a temperature of air in the first and second chambers, respectively, and programming a memory in the control system with a set of instructions to measure the air pressure and the temperature in each of the first and second chambers before and after the air transfer between the first and second chambers, store the pressure and temperature values from the first and second pressure sensors and the first and second temperature sensors before and after the air transfer between the first and second chambers, and determine a non-displaced volume of air in the first chamber relative to the second volume from the pressures and temperatures of each of the first and second chambers before and after the air transfer between the first and second chambers.

20. The method of claim 18, further comprising forming or attaching a gasket, seal or molding on a surface of one of the door and the first chamber facing the other of the door and the first chamber, wherein the gasket, seal or molding is configured to make the first chamber airtight when the door is closed and the pressure inside the first chamber changes by 3-5%.

* * * * *